(12) United States Patent
Chodkowski et al.

(10) Patent No.: US 11,083,861 B2
(45) Date of Patent: Aug. 10, 2021

(54) CUSHION WITH PROTRUSION AND PATIENT INTERFACE DEVICE INCLUDING SAME

(71) Applicant: KONINKLIJKE PHILIPS N.V., Eindhoven (NL)

(72) Inventors: Lauren Patricia Chodkowski, Pittsburgh, PA (US); Robert William Baiko, Pittsburgh, PA (US); Jonathan Sayer Grashow, Cheswick, PA (US)

(73) Assignee: Koninklijke Philips N.V., Eindhoven (NL)

( * ) Notice: Subject to any disclaimer, the term of this patent is extended or adjusted under 35 U.S.C. 154(b) by 393 days.

(21) Appl. No.: 16/139,198

(22) Filed: Sep. 24, 2018

(65) Prior Publication Data

US 2019/0091428 A1 Mar. 28, 2019

Related U.S. Application Data

(60) Provisional application No. 62/564,309, filed on Sep. 28, 2017.

(51) Int. Cl.
   *A61M 16/06* (2006.01)

(52) U.S. Cl.
   CPC ........ *A61M 16/0622* (2014.02); *A61M 16/06* (2013.01); *A61M 16/0666* (2013.01);
   (Continued)

(58) Field of Classification Search
   CPC ................ A41D 13/0025; A41D 13/11; A41D 13/1153; A41D 13/1184; A41D 13/1209; A41D 13/1218; A42B 1/046; A42B 3/286; A42B 90/40; A61M 11/00; A61M 15/00; A61M 15/0016; A61M 15/0018; A61M 16/0003; A61M 16/0006; A61M 16/0057; A61M 16/0066; A61M 16/0069; A61M 16/009; A61M 16/0096; A61M 16/06; A61M 16/0605; A61M 16/0611;
   (Continued)

(56) References Cited

U.S. PATENT DOCUMENTS

| 3,529,594 A | * | 9/1970 | Charnley | ........... | A41D 13/0025 128/863 |
| 3,990,112 A | * | 11/1976 | Ciffolillo | ............... | A41D 13/11 2/424 |

(Continued)

FOREIGN PATENT DOCUMENTS

EP 2481434 A2 8/2012

*Primary Examiner* — Annette Dixon
(74) *Attorney, Agent, or Firm* — Michael W. Haas (57) ABSTRACT

A cushion is for use in a pressure support system for delivering a flow of breathing gas to an airway of a patient. The cushion includes a body having a first end and a second end located opposite the first end. The body defines a space therein. The cushion further includes a sealing portion defining a single opening into the space. The single opening is adapted to surround both a first nostril and a second nostril of a patient. The sealing portion is located between the first end and the second end. The sealing portion includes a first protruding portion and a second protruding portion each extending outwardly from the body and being adapted to sealingly engage against an interior surface of a corresponding one of the first nostril and the second nostril.

13 Claims, 10 Drawing Sheets

(52) U.S. Cl.
CPC . *A61M 16/0683* (2013.01); *A61M 2210/0618* (2013.01); *A61M 2210/0625* (2013.01)

(58) Field of Classification Search
CPC .......... A61M 16/0616; A61M 16/0622; A61M 16/0627; A61M 16/0633; A61M 16/0666; A61M 16/0672; A61M 16/0677; A61M 16/0683; A61M 16/0688; A61M 16/0694; A61M 16/08; A61M 16/0816; A61M 16/0825; A61M 16/0833; A61M 16/0841; A61M 16/0858; A61M 16/0875; A61M 16/083; A61M 16/10; A61M 16/101; A61M 16/1045; A61M 16/107; A61M 16/109; A61M 16/125; A61M 16/127; A61M 16/16; A61M 16/20; A61M 16/201; A61M 16/208; A61M 2016/0015; A61M 2016/0021; A61M 2016/0024; A61M 2016/0027; A61M 2016/0039; A61M 2016/0661; A61M 2202/0007; A61M 2202/0085; A61M 2202/0208; A61M 2202/0225; A61M 2202/03; A61M 2202/30; A61M 2205/02; A61M 2205/0205; A61M 2205/0216; A61M 2205/0227; A61M 2205/0238; A61M 2205/0272; A61M 2205/15; A61M 2205/17; A61M 2205/273; A61M 2205/3334; A61M 2205/3375; A61M 2205/3569; A61M 2205/3592; A61M 2205/3613; A61M 2205/3653; A61M 2205/50; A61M 2205/581; A61M 2205/582; A61M 2205/583; A61M 2205/588; A61M 2205/59; A61M 2205/6045; A61M 2205/6054; A61M 2205/6063; A61M 2205/8206; A61M 2205/84; A61M 2207/00; A61M 2207/10; A61M 2209/06; A61M 2209/088; A61M 2210/0618; A61M 2210/0625; A61M 2230/40; A61M 2230/432; A61M 2250/00; A61M 39/08; A42C 5/04; A61F 9/029; H04R 1/1083; H04R 5/0335; Y10S 128/26; Y10S 128/91; A62B 17/006; A62B 18/006; A62B 18/025; A62B 23/06

See application file for complete search history.

(56) References Cited

U.S. PATENT DOCUMENTS

| | | | | |
|---|---|---|---|---|
| 4,406,283 | A * | 9/1983 | Bir | A61M 16/0683 128/207.18 |
| 4,803,981 | A * | 2/1989 | Vickery | A61M 16/06 128/206.24 |
| 5,526,806 | A * | 6/1996 | Sansoni | A61M 16/0666 128/206.11 |
| 6,119,694 | A * | 9/2000 | Correa | A61M 16/0666 128/207.13 |
| 9,095,673 | B2 | 8/2015 | Barlow | |
| 9,162,034 | B2 * | 10/2015 | Veliss | A61M 16/0605 |
| 9,764,107 | B2 * | 9/2017 | Grashow | A61M 16/0816 |
| 9,981,103 | B2 * | 5/2018 | Eury | A61M 16/0622 |
| 2008/0060653 | A1 | 3/2008 | Hallett | |
| 2013/0220327 | A1 | 8/2013 | Barlow | |
| 2015/0182719 | A1 * | 7/2015 | Grashow | A61M 16/0666 128/205.25 |
| 2015/0352308 | A1 | 12/2015 | Cullen | |
| 2016/0082216 | A1 | 3/2016 | Lynch et al. | |
| 2018/0264218 | A1 | 9/2018 | Chodkowski | |
| 2020/0054850 | A1 * | 2/2020 | Davidson | A61M 16/0816 |
| 2020/0330712 | A1 * | 10/2020 | Henry | A61M 16/0694 |

* cited by examiner

CUSHION WITH PROTRUSION AND PATIENT INTERFACE DEVICE INCLUDING SAME

CROSS-REFERENCE TO RELATED APPLICATIONS

This patent application claims the priority benefit under 35 U.S.C. § 119(e) of U.S. Provisional Application No. 62/564,309, filed on Sep. 28, 2017, the contents of which are herein incorporated by reference.

BACKGROUND OF THE INVENTION

1. Field of the Invention

The present invention relates to cushions for use in a patient interface device. The present invention also relates to patient interface devices such as, for example, patient interface devices for use in a pressure support system.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway, typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

FIGS. 1-4, for example, show a traditional cradle style cushion 10 that is structured to sealingly engage against a pair of nostrils of a patient. As shown most clearly in FIGS. 2 and 3, cushion 10 has a body 12 and a sealing portion 14. Sealing portion 14 has an edge portion 16 that defines an opening. Edge portion 16 is structured to surround each of the nostrils of the patient such that when employed in a patient interface device, breathing gas enters each of the patient's nostrils through the single opening. Continuing to refer to FIG. 3, sealing portion 14 is generally a single convex surface that is structured to seal against the outside of the patient's nostrils. As a result, cushion 10 is required to be relatively large because providing a proper seal typically requires the entire sealing portion 14 to engage the outside of the patient's nostrils. See FIG. 4, for example, which depicts sealing portion 14 of cushion 10 sealingly engaged against an outside of a patient's nostrils. This configuration creates problems associated with comfort. Furthermore, by being relatively large, cushion 10 is less stable when worn by a patient because objects such as pillows have a greater likelihood of engaging and dislodging cushion 10 from its proper therapeutic position on the face of the patient.

SUMMARY OF THE INVENTION

Accordingly, it is an object of the present invention to provide an improved cushion and patient interface device employing the same.

As one aspect of the disclosed concept, a cushion is provided for use in a pressure support system for delivering a flow of breathing gas to an airway of a patient. The cushion includes a body having a first end and a second end located opposite the first end. The body defines a space therein. The cushion further includes a sealing portion defining a single opening into the space. The single opening is adapted to surround both a first nostril and a second nostril of a patient. The sealing portion is located between the first end and the second end. The sealing portion includes a first protruding portion and a second protruding portion each extending outwardly from the body and being adapted to sealingly engage against an interior surface of a corresponding one of the first nostril and the second nostril.

As another aspect of the disclosed concept, a cushion is provided for use in a pressure support system for delivering a flow of breathing gas to an airway of a patient. The cushion includes a body having a first end and a second end located opposite the first end. The body defines a space therein. The cushion further includes a sealing portion defining a single opening into the space, the single opening being adapted to surround both a first nostril and a second nostril of a patient. The sealing portion is located between the first end and the second end. The sealing portion includes an edge portion defining the opening, the edge portion having a first concave portion, a second concave portion, and a convex portion extending between the first concave portion and the second concave portion. The first concave portion is structured to seal against an interior surface of the first nostril. The second concave portion is structured to seal against an interior surface of the second nostril.

As another aspect of the disclosed concept, a patient interface device is provided for use in a pressure support system. The pressure support system includes a gas flow generator structured to generate a flow of breathing gas to be delivered to an airway of a patient. The patient interface device includes either of the aforementioned cushions, and a conduit coupled to the first end of the cushion and structured to be coupled to the gas flow generator. The conduit is structured to provide a passage for the flow of breathing gas from the gas flow generator to the first end of the cushion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly (i.e., one part is positioned in or directly on another part) or indirectly (i.e., through one or more intermediate parts or components), so long as a link occurs. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As employed herein, the term "sealing portion" shall refer to a portion of a cushion that is structured to sealingly engage a patient when the cushion is employed to deliver therapy to the patient. As used herein, the phrase "sealingly engage" shall mean elements which contact each other in a manner such that a generally air-tight seal is formed therebetween.

Figure 1:
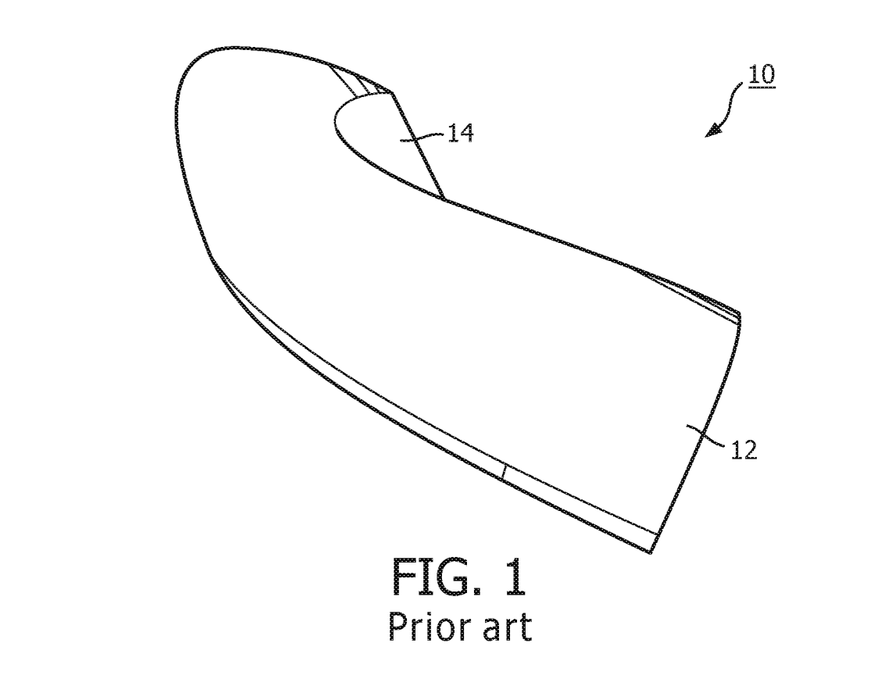
FIGS. 1-3 are front isometric, rear isometric, and front views, respectively, of a traditional cushion.
Figure 2:
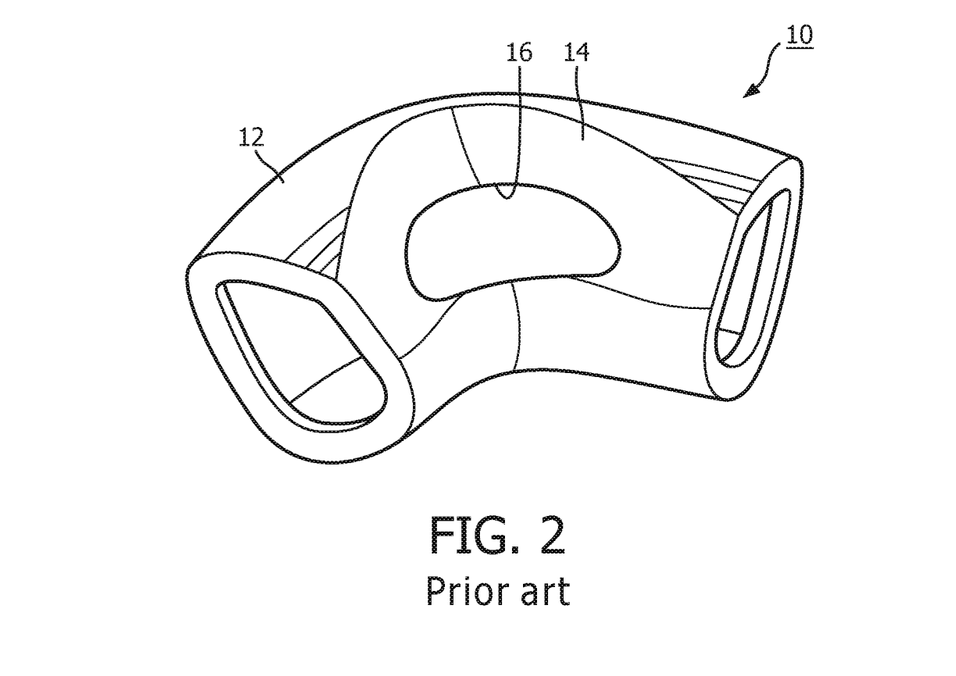
Figure 3:
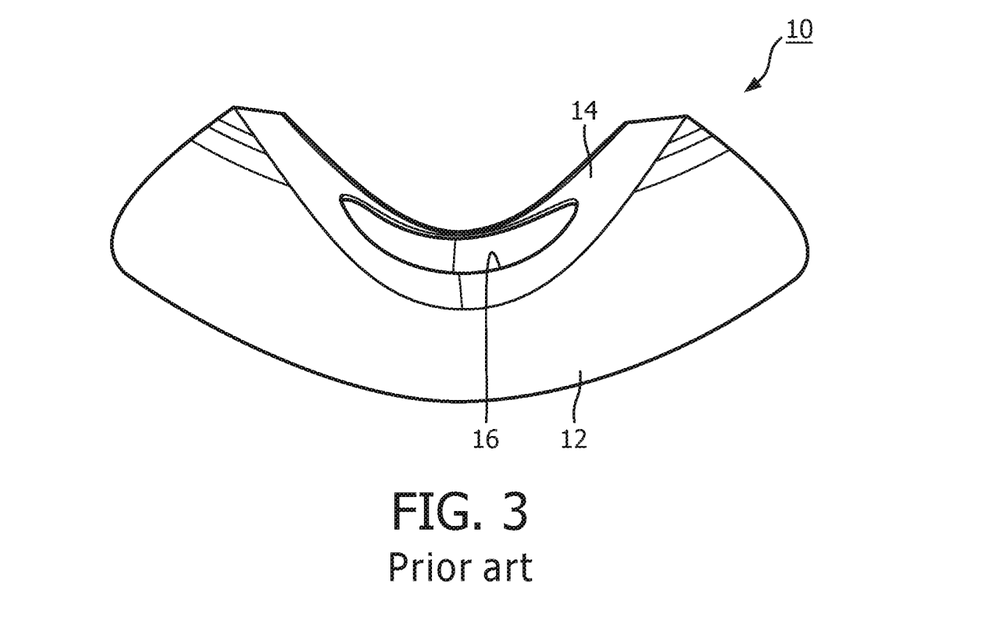
Figure 4:
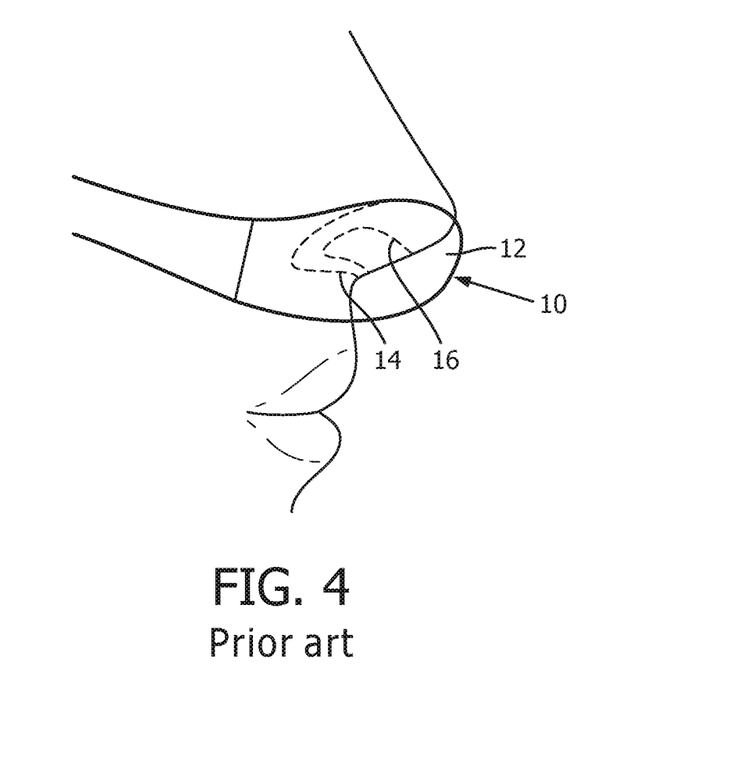
FIG. 4 is an isometric view of the cushion of FIGS. 1-3, shown as employed on a patient.
Figure 5:
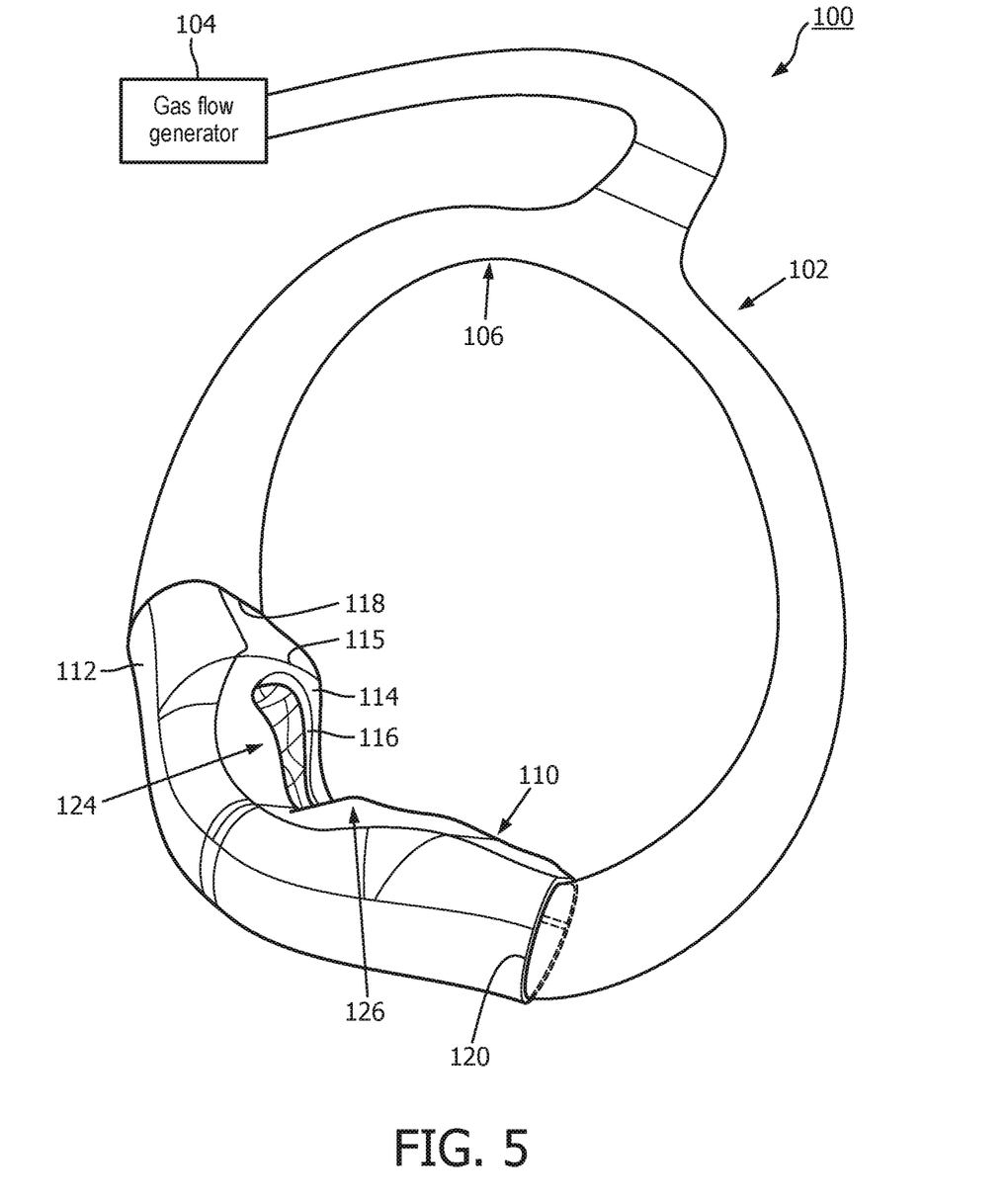
FIG. 5 is a partially simplified front isometric view of a pressure support system, in accordance with one non-limiting embodiment of the disclosed concept.
Figure 6:
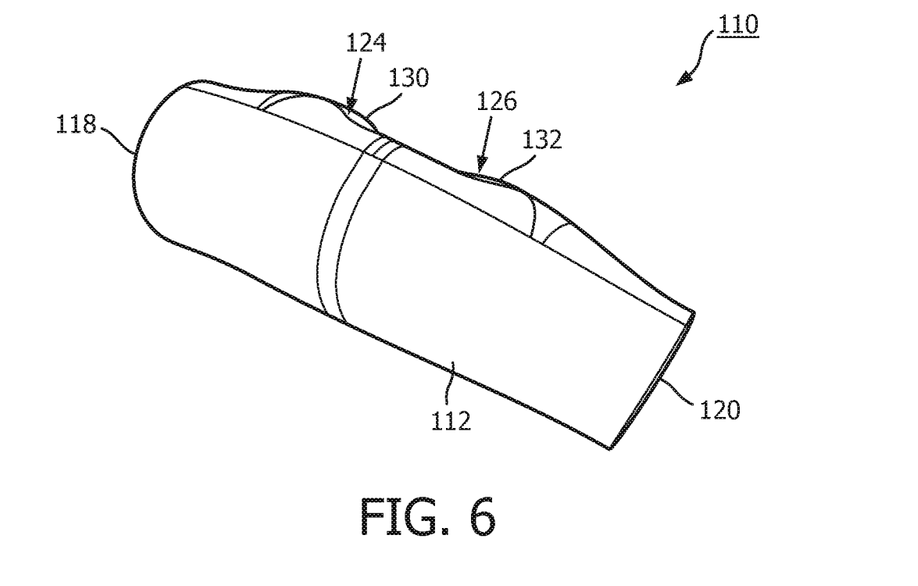
FIG. 6 is a front isometric view of a cushion for the pressure support system of FIG. 4.

FIG. 5 is a partially simplified view of a pressure support system 100, in accordance with one non-limiting embodiment of the disclosed concept. Pressure support system 100 includes a patient interface device 102 and a gas flow generator 104 (shown in simplified form). Patient interface device 102 includes a conduit 106 (shown in simplified form) and a novel cushion 110 coupled to conduit 106. In one example embodiment, conduit 106 forms a portion of a headgear (e.g., without limitation, wherein opposing arms of conduit 106 extend along left and right sides of a face of a patient). Gas flow generator 104 is structured to generate a flow of breathing gas to be delivered to an airway of the patient. Specifically, conduit 106 is structured to communicate the flow of breathing gas from gas flow generator 104 to cushion 110, which correspondingly is adapted to communicate the flow of gas to the airway of the patient.

FIGS. 6-9 show different views of cushion 110. Cushion 110 may be made of any suitable material in the art (e.g., without limitation, silicone). Cushion 110 has a body 112 and a sealing portion 114. Body 112 has a first end 118 and a second end 120 located opposite first end 118. Body 112 further defines a space therein for receiving a flow of breathing gas from gas flow generator 104. In one example embodiment, body 112 defines a passage through first end 118 and second end 120. For example and without limitation, as shown in FIG. 5, conduit 106 is preferably coupled to first end 118 and second end 120 of body 112 in order to provide a passage for the flow of breathing gas from gas flow generator 104 to first end 118 and also to second end 120 of cushion 110 (i.e., and thus to the airway of the patient).

Referring again to FIGS. 7 and 8, sealing portion 114, which is located between first and second ends 118,120, has a peripheral portion 115 and an edge portion 116 located internal with respect to peripheral portion 115. Peripheral portion 115 defines an outermost boundary of sealing portion 114. Edge portion 116 is spaced from body 112 and defines a single opening 117 into the interior space of body 112, a single opening 117 which is structured to surround a first and second nostril of a patient. In one example embodiment, edge portion 116 is not structured to surround a mouth of a patient. However, it is within the scope of the disclosed concept for a suitable alternative cushion to seal against the interior surfaces of a patient's nostrils in a similar manner as cushion 110, and also be adapted to surround a patient's mouth (i.e., be a full face cushion). For example and without limitation, such a cushion could have an edge portion similar to edge portion 116 of cushion 110, and have a separate edge portion adapted to surround the patient's mouth. Such a cushion could also have one continuous edge portion partially similar to edge portion 116 (i.e., proximate the nostrils), but be adapted to also surround the patient's mouth.

Figure 7:
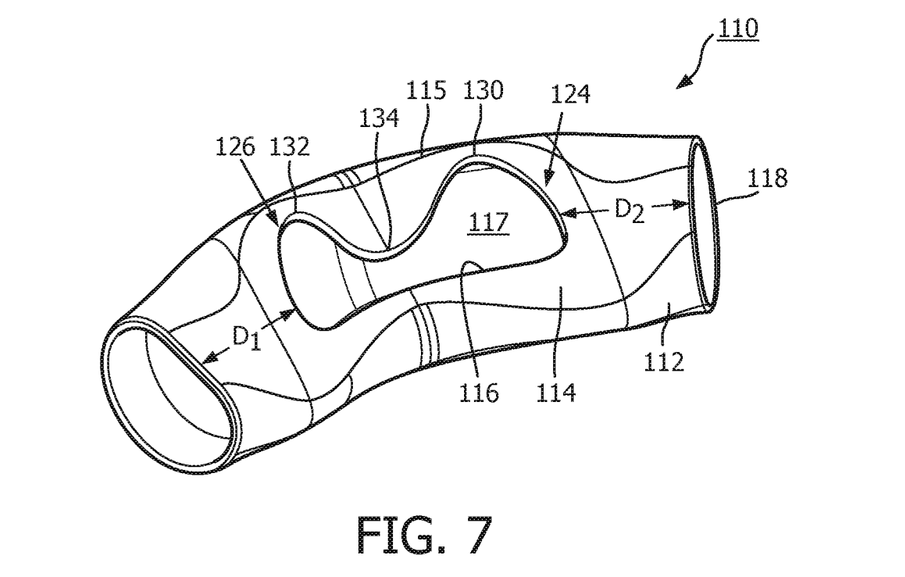
FIGS. 7-9 are rear isometric, back, and front views, respectively, of the cushion of FIG. 6.
Figure 8:
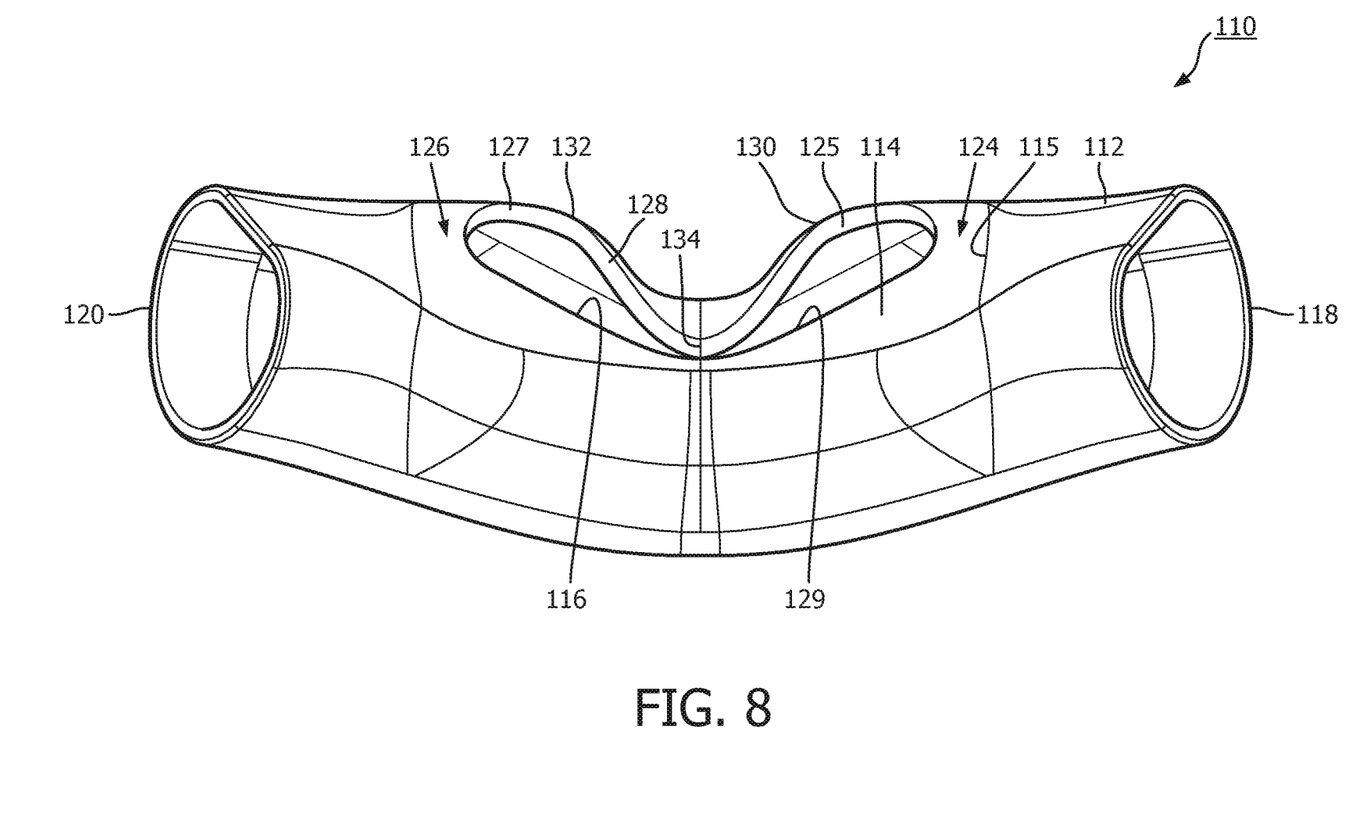

In one example embodiment, edge portion 116 is spaced a first distance $D_1$ from first end 118 of body 112, and a second distance $D_2$ from second end 120 of body 112, wherein first distance $D_1$ is the same as second distance $D_2$. Edge portion 116 is further not circular-shaped. As such, cushion 110 is different from traditional pillows style cushions, which have two separate circular-shaped openings, each structured to seal against a separate nostril of a patient.

Additionally, in accordance with the disclosed concept, cushion 110 is different from traditional cradle style cushions, such as cushion 10, depicted in FIGS. 1-4. More specifically, sealing portion 114 of cushion 110 includes a first protruding portion 124 and a second protruding portion 126, each extending outwardly from body 112 and being adapted to sealingly engage an interior surface of a corresponding first and second nostril of a patient. As discussed above in the Background section, sealing portion 14 of cushion 10 is generally one continuous convex surface that is adapted to seal against the outside of the patient's nostrils. The novel geometry of sealing portion 114 advantageously allows cushion 110 to have a smaller footprint than prior art cushions (e.g., without limitation, cradle style cushion 10 and traditional pillows style cushions), as will be discussed below.

As shown most clearly in FIG. 8, the geometry of edge portion 116 is not a single convex portion, like edge portion 16 (FIGS. 1-4) of cushion 10. Rather, in one example embodiment, edge portion 116 has a first concave portion 125, a second concave portion 127, a first convex portion 128 extending between first and second concave portions 125,127, and a second convex portion 129. Second convex portion 129 is also located on an opposite side of opening 117 and spaced from first convex portion 128, and extends between first and second concave portions 125,127. First concave portion 125 coincides with first protruding portion 124, and second concave portion 127 coincides with second protruding portion 126. It will be appreciated that first and second concave portions 125,127 are each adapted to separately seal against a portion of the interior surface of corresponding first and second nostrils of a patient.

Figure 9:
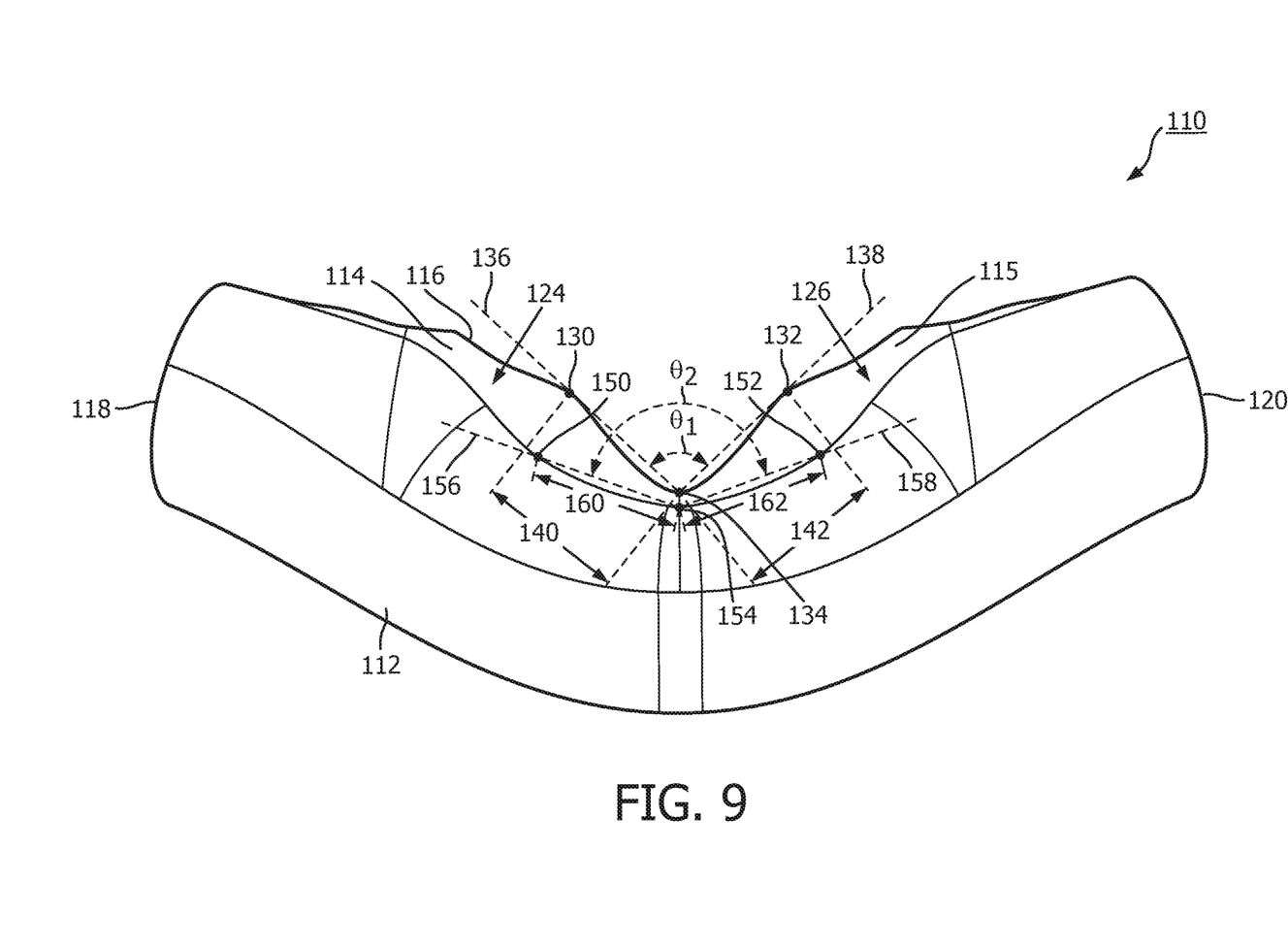

The minimized footprint of cushion 110 can also be appreciated by referring to FIG. 9. As shown, edge portion 116 has a first peak point 130 located in first protruding portion 124, a second peak point 132 located in second protruding portion 126, a bottom point 134 located midway between first peak point 130 and second peak point 132, a first axis 136 extending through first peak point 130 and bottom point 134, and a second axis 138 extending through second peak point 132 and bottom point 134. First peak point 130 is spaced a first distance 140 from bottom point 134. Second peak point 132 is spaced a second distance 142 from bottom point 134. First axis 136 is located at a first angle $\theta_1$ with respect to second axis 138.

Continuing to refer to FIG. 9, peripheral portion 115 has a first location 150 located proximate first peak point 130, a second location 152 located proximate second peak point 132, a middle location 154 located proximate bottom point 134 and midway between first location 150 and second location 152, a third axis 156 extending through first location 150 and middle location 154, and a fourth axis 158 extending through second location 152 and middle location 154. First location 150 is spaced a third distance 160 from middle location 154. Second location 152 is spaced a fourth distance 162 from middle location 154. First distance 140 is the same as third distance 160. Second distance 142 is the same as fourth distance 162. Third axis 156 is located at a second angle $\theta_2$ with respect to fourth axis 158. As shown, first angle $\theta_1$ is less than second angle $\theta_2$. In one example embodiment, first angle $\theta_1$ is between 90 degrees and 120 degrees, and second angle $\theta_2$ is less than 180 degrees.

As disclosed herein, cushion 110 is generally symmetric about a central plane separating protruding portions 124,126 from each other. However, it will be appreciated that suitable alternative cushions (not shown) are contemplated wherein protruding portions are not symmetrical to each other. For example and without limitation, it is contemplated that cushions may be customized to features of the faces of particular patients. As such, it is understood that on some patients, and thus in some cushions, the right protruding portion may protrude outwardly a greater or lesser amount, and in a different direction, than the right protruding portion, in order to properly seal to a given patients nose. Furthermore, as a suitable alternative cushion may be customized, $\theta_1$ and $\theta_2$ for the alternative cushion may be different values in order to accommodate the facial geometry of the patient.

In this manner, first and second protruding portions 124, 126 provide a mechanism by which sealing portion 114 can seal against the interior surfaces of the nostrils of the patient, thereby allowing for a reduced footprint. As such, it will be appreciated that when patient interface device 102 is donned by the patient, first and second protruding portions 124,126 are each structured to be inflated in order to sealingly engage against the interior surfaces of patient's nostrils. Furthermore, body 112 is structured to sealingly engage across the upper lip of the patient via a compression seal. Cushion 110 thus provides a mechanism to transition from an interior nostril seal to an upper lip seal. In other words, the seal of cushion 110 is a hybrid in that contacts the patient's face on the interior of the nostrils, and also on the outside of the face across the upper lip of the patient.

Figure 10:
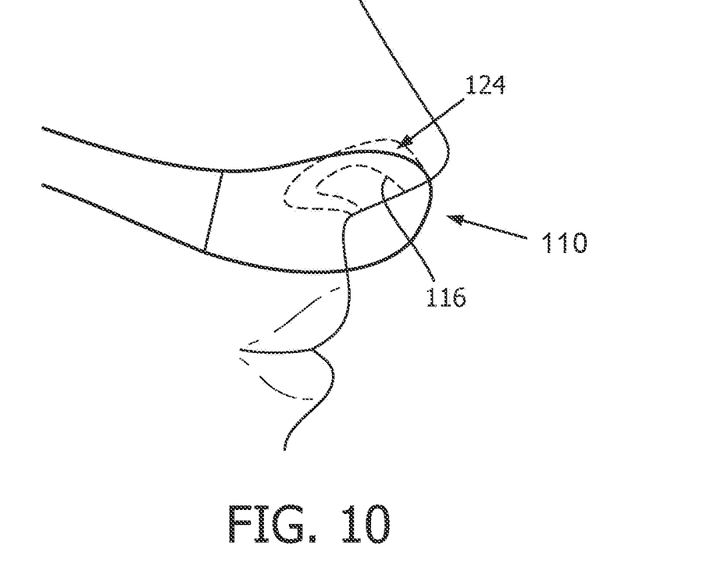
FIG. 10 is a front isometric view of the cushion of FIGS. 6-9, shown as employed on a patient.

Accordingly, unlike cushion 10 (FIGS. 1-4) which has a single convex surface (i.e., from the orientation of FIG. 3) extending from a peripheral portion directly across sealing portion 14, protruding portions 124,126 of cushion 110 extend upwardly and outwardly from body 112, thereby allowing for a seal to be realized with the interior of the nostrils of the patient. Compare, for example, FIG. 10, in which protruding portion 124 extends into the interior of the patient's nostril, and FIG. 4, in which prior art sealing portion 14 does not extend into the interior of the patient's nostril. It will thus be appreciated that cushion 10 (FIGS. 1-4), which has no such protruding portions, thus has a significantly larger footprint that is required to seal against the outside of the nostrils of the patient. Compare, for example, FIG. 3 to FIG. 9. By having the reduced footprint, cushion 110 is advantageously able to be more stable when secured to a patient during therapy. That is, cushion 110, by being relatively small, is less likely to make contact with objects, such as a pillow, during therapy, objects that might otherwise cause cushion 110 to move and/or be dislodged from the proper therapeutic position. Furthermore, cushion 110 also reduces the impedance of the patient's field of view.

Figure 11:
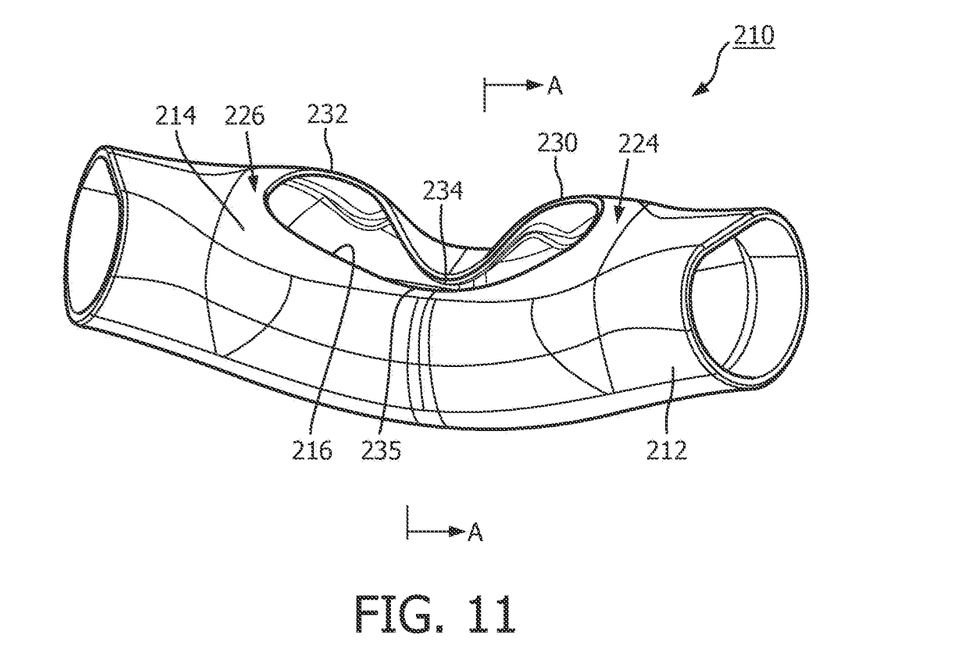
FIGS. 11 and 12 are different rear isometric views of another cushion, in accordance with another non-limiting embodiment of the disclosed concept.
Figure 12:
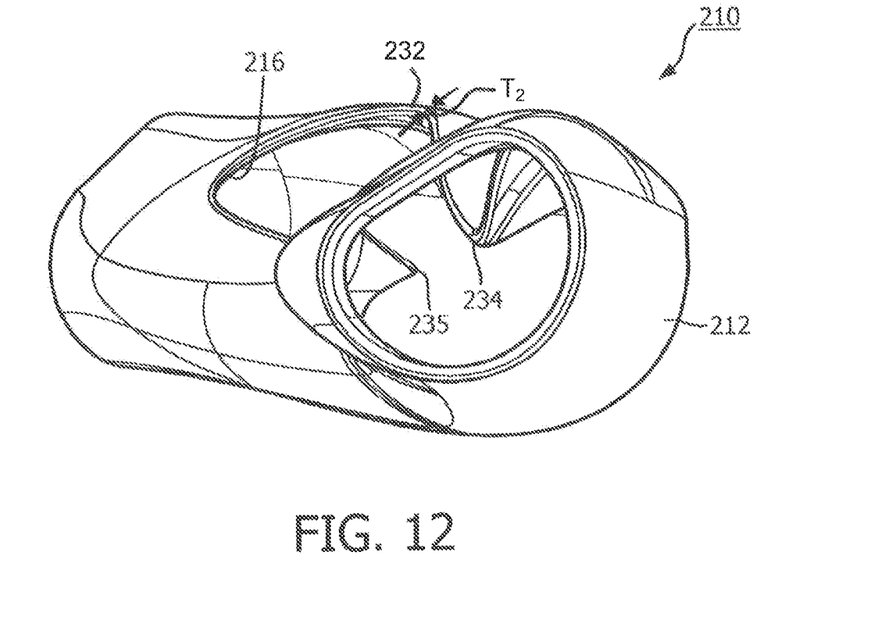
Figure 13:
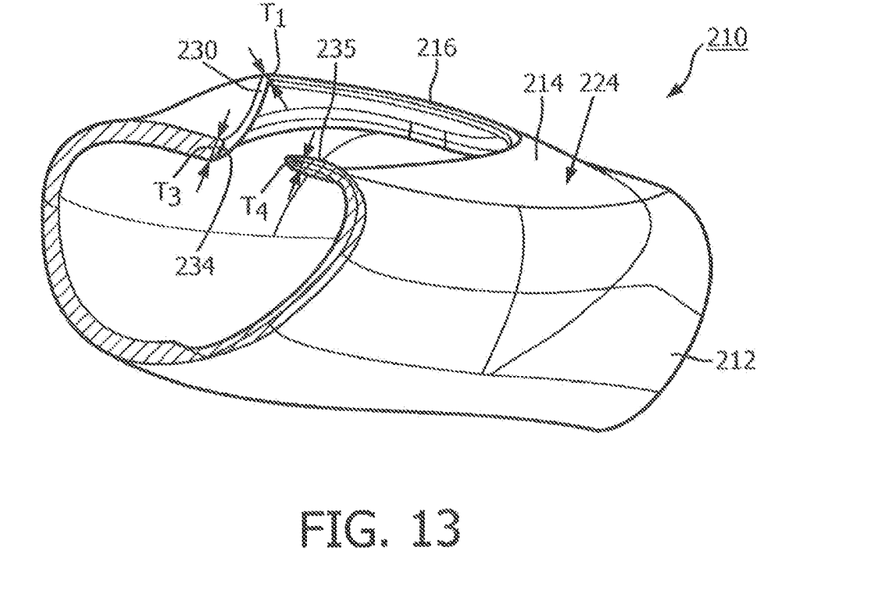
FIG. 13 is a section view of the cushion of FIGS. 11 and 12, taken along line A-A of FIG. 11.

FIGS. 11-13 show different views of another cushion 210, in accordance with another non-limiting embodiment of the disclosed concept. Cushion 210 may be substituted into pressure support system 100 (FIG. 5) in place of cushion 110. Furthermore, cushion 210 is structured similar to (i.e., has a body 212 and a sealing portion 214 having protruding portions 224,226), and provides similar advantages as, cushion 110, discussed above. As such, like reference numbers will be used herein to designate like features.

However, unlike cushion 110, cushion 210 has a number of thinned portions to allow for a stronger seal with the nostrils of the patient. More specifically, as shown in FIG. 13, which is a section view of FIG. 11, edge portion 216 has a first thickness $T_1$ proximate first peak point 230. Shown in FIG. 12, edge portion 216 has a second thickness $T_2$ proximate second peak point 232. Referring again to FIG. 13, edge portion has a first bottom point 234 located midway between first and second peak points 230,232, and a second bottom point 235 opposite first bottom point 234 and directly between first and second protruding portions 224, 226. As shown in FIG. 13, edge portion 216 has a third thickness $T_3$ proximate first bottom point 234, and a fourth thickness $T_4$ proximate second bottom point 235. First thickness $T_1$, second thickness $T_2$ (shown in FIG. 12) proximate second peak point 232, and fourth thickness $T_4$ are less than third thickness $T_3$. By having reduced thicknesses in protruding portions 224,226, as discussed and shown in FIGS. 11-13, protruding portions are advantageously able to inflate/expand more during therapy. This results in greater contact between sealing portion 214 and the interior surfaces of the nostrils of the patient. In other words, the thinned regions translate into an improved seal.

Figure 14:
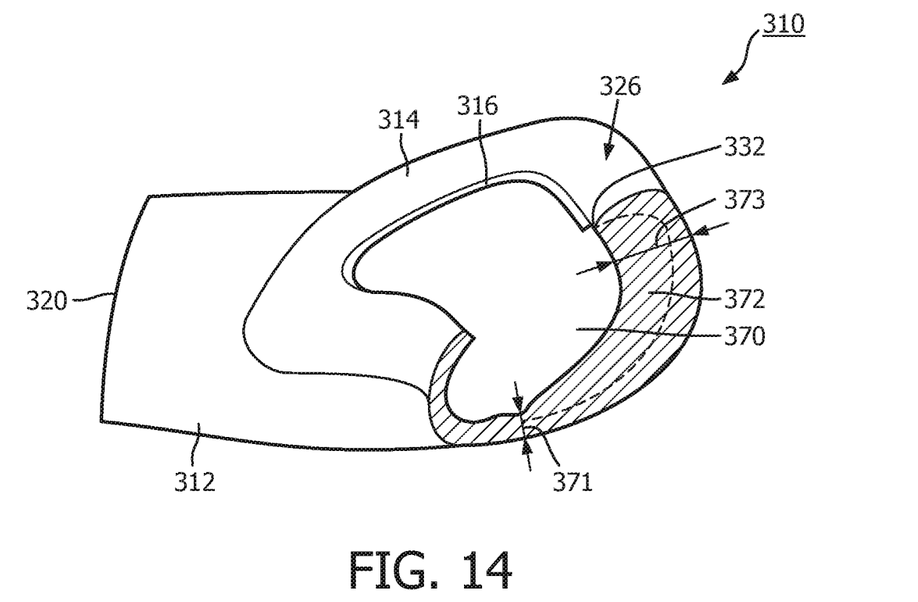
FIG. 14 is a section view of another cushion, in accordance with another non-limiting embodiment of the disclosed concept.

FIG. 14 shows a section view of a portion of another cushion 310 that may be substituted into pressure support system 100 (FIG. 5) for cushion 110, in accordance with another non-limiting embodiment of the disclosed concept. Cushion 310 is structured similar to (i.e., has a sealing portion 314 having protruding portions (only one protruding portion 326 is shown)), and provides similar advantages as, cushions 110,210, discussed above. As such, like reference numbers will be used herein to designate like features.

Body 312 of cushion 310 has a middle region 370 located opposite edge portion 316 and midway between first end (not shown) and second end 320 of body 312. Additionally, cushion 310 further includes a support rib 372 extending from proximate second peak point 332 to middle region 370 in order to provide support for second protruding portion 326. It will be appreciated that cushion 310 further includes another support rib (not shown) extending from first peak point (not shown in FIG. 14) to middle region 370 in order to provide support to the first peak point. Support ribs 372 (i.e., and the other support rib for the first peak point (not shown)) are thickened regions which allow cushion 310 to place increased pressure on the front of the nostrils. For example, as shown, the wall of cushion 310 proximate middle region 370 has a first thickness 371, and the wall of cushion 310 proximate support rib 372 has a second thickness 373 greater than first thickness 371.

Figure 15:
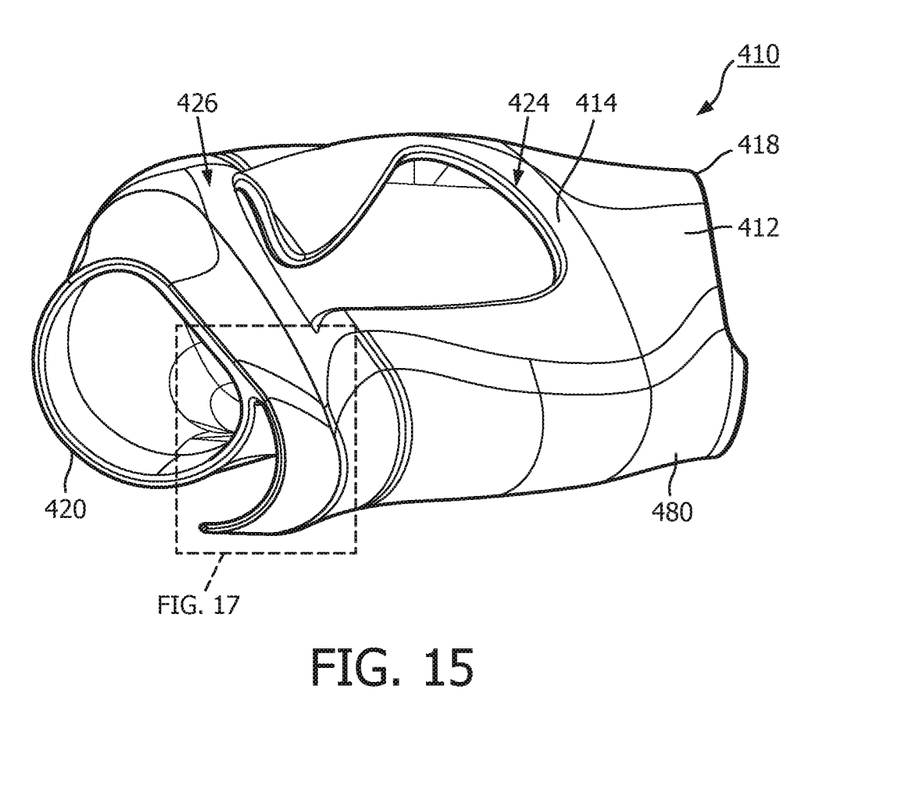
FIGS. 15 and 16 are rear isometric and bottom isometric views, respectively, of another cushion, in accordance with another non-limiting embodiment of the disclosed concept.
Figure 16:
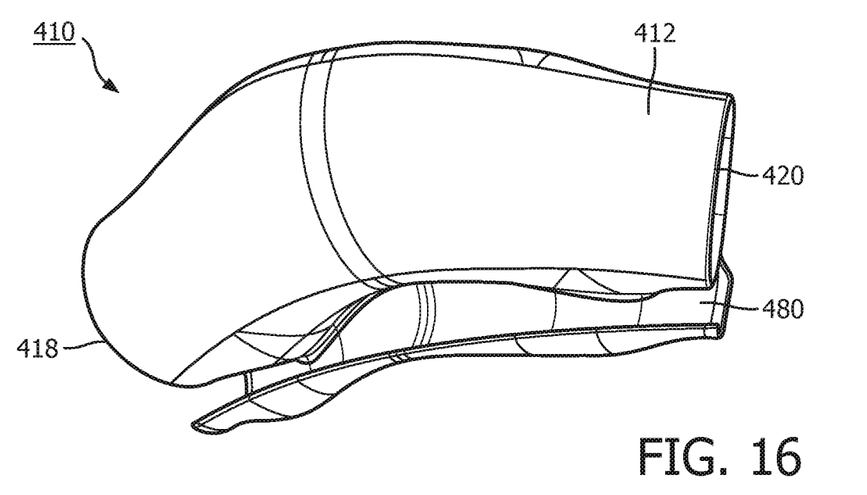
Figure 17:
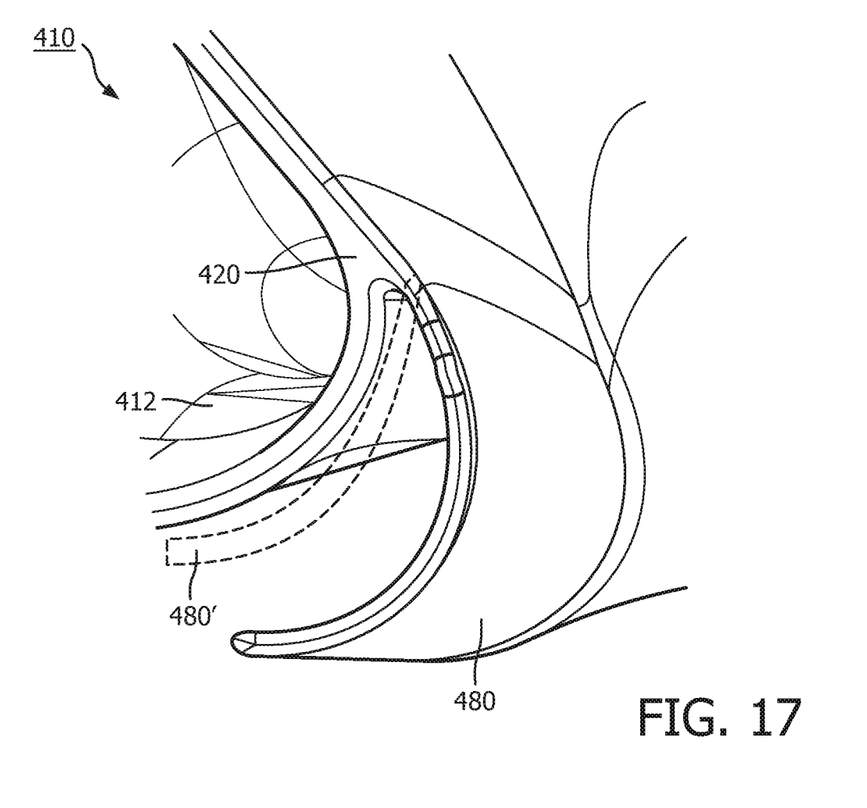
FIG. 17 is an enlarged view of the portion of the cushion of FIG. 15 as indicated in FIG. 15.

FIGS. 15-17 show different views of another cushion 410 that may be substituted into pressure support system 100 (FIG. 5) for cushion 110, in accordance with another non-limiting embodiment of the disclosed concept. Cushion 410 is structured similar to (i.e., has a sealing portion 414 having protruding portions 424,426), and provides similar advantages as, cushions 110,210,310, discussed above. As such, like reference numbers will be used herein to designate like features.

In accordance with the disclosed concept, cushion 410 includes an upper lip spring 480 extending outwardly from body 412. In one example embodiment, upper lip spring 480 extends from first end 418 of body 412 to second end 420 of body 412. Referring to the enlarged view of FIG. 17, upper lip spring 480 is structured to move between a first position corresponding to disengagement with an upper lip of a patient, and a second position (shown in dashed line drawing in FIG. 17 and indicated with reference numeral 480') corresponding to engagement with an upper lip of a patient. When upper lip spring 480 moves from the first position toward the second position, upper lip spring 480 moves toward body 412. Furthermore, because upper lip spring 480 is biased toward the first position, when cushion 410 is donned by a patient, upper lip spring 480 provides a novel mechanism by which the pressure of cushion 410 on the face of the patient can be evenly distributed across the patient's upper lip. Furthermore, when cushion 410 is donned by a patient, upper lip spring 480 may assist with ensuring that protruding portions 424,426 become wedged into the interior of the patient's nostrils.

Accordingly, it will be appreciated that the disclosed concept provides for an improved (e.g., without limitation, relatively small footprint, more stable) cushion 110, 210, 310, 410 and patient interface device 102 including the same, in which a sealing portion 114, 214, 314, 414, which has a single opening 117 adapted to surround both nostrils of a patient, further has a number of protruding portions 124, 126, 224, 226, 326, 424, 426 each adapted to sealingly engage against the interior surface of a corresponding nostril of a patient.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion for use in a pressure support system for delivering a flow of breathing gas to an airway of a patient, the cushion comprising:
   a body comprising a first end and a second end disposed opposite the first end, the body defining a space therein; and
   a sealing portion defining a single opening into the space, the single opening being adapted to surround both a first nostril and a second nostril of a patient, the sealing portion being disposed between the first end and the second end, the sealing portion comprising a first protruding portion and a second protruding portion each extending outwardly from the body and being adapted to sealingly engage against an interior surface of a corresponding one of the first nostril and the second nostril,
   wherein the sealing portion has an edge portion defining the single opening, wherein the edge portion has a first peak point disposed in the first protruding portion, a second peak point disposed in the second protruding portion, and a bottom point disposed midway between the first peak point and the second peak point, wherein the edge portion has a first thickness proximate the first peak point, a second thickness proximate the second peak point, and a third thickness proximate the bottom point, and wherein the first thickness and the second thickness are less than the third thickness.

2. The cushion according to claim 1, wherein the edge portion further has a second bottom point disposed opposed the bottom point and directly between the first protruding portion and the second protruding portion, wherein the edge portion has a fourth thickness proximate the second bottom point, and wherein the fourth thickness is less than the third thickness.

3. The cushion according to claim 1, wherein the body further comprises a middle region disposed opposite the edge portion and midway between the first end and the second end, wherein the cushion further comprises a first support rib extending from proximate the first peak point to the middle region in order to provide support to the first protruding portion, and wherein the cushion further comprises a second support rib extending from proximate the second peak point to the middle region in order to provide support to the second protruding portion.

4. The cushion according to claim 1, wherein the sealing portion has an edge portion defining the single opening, wherein the edge portion is spaced a first distance from the first end of the cushion, wherein the edge portion is spaced a second distance from the second end of the cushion, wherein the first distance is the same as the second distance, wherein the body of the cushion is structured to sealingly engage across an upper lip of the patient via a compression seal.

5. The cushion according to claim 1, wherein the cushion further comprises an upper lip spring extending outwardly from the body, the upper lip spring being structured and positioned to engage an upper lip of a patient, wherein the upper lip spring is structured to move between a first position corresponding to disengagement with the upper lip of the patient, and a second position corresponding to engagement with the upper lip of the patient, wherein the upper lip spring is biased toward the first position, and wherein, when the upper lip spring moves from the first position toward the second position, the upper lip spring moves toward the body.

6. The cushion according to claim 5, wherein the upper lip spring extends from the first end of the body to the second end of the body.

7. The cushion according to claim 1, wherein the sealing portion has a peripheral portion and the edge portion disposed internal with respect to the peripheral portion, wherein the peripheral portion defines an outermost boundary of the sealing portion, wherein the edge portion defines the single opening and is spaced from the body, a first axis extending through the first peak point and the bottom point, and a second axis extending through the second peak point and the bottom point, wherein the first peak point is spaced a first distance from the bottom point, wherein the second peak point is spaced a second distance from the bottom point, wherein the first axis is disposed at a first angle ($\theta_1$) with respect to the second axis, wherein the peripheral portion has a first location disposed proximate the first peak point, a second location disposed proximate the second peak point, a middle location disposed proximate the bottom point and midway between the first location and the second location, a third axis extending through the first location and the middle location, and a fourth axis extending through the second location and the middle location, wherein the first location is spaced a third distance from the middle location, wherein the second location is spaced a fourth distance from the middle location, wherein the first distance is the same as the third distance, wherein the second distance is the same as the fourth distance, wherein the third axis is disposed at a second angle ($\theta_2$) with respect to the fourth axis, and wherein the first angle is less than the second angle.

8. The cushion according to claim 7, wherein the first angle is between 90 degrees and 120 degrees.

9. A cushion for use in a pressure support system for delivering a flow of breathing gas to an airway of a patient, the cushion comprising:
   a body comprising a first end and a second end disposed opposite the first end, the body defining a space therein; and
   a sealing portion defining a single opening into the space, the single opening being adapted to surround both a first nostril and a second nostril of a patient, the sealing portion being disposed between the first end and the second end, the sealing portion comprising an edge portion defining the opening, the edge portion having a first concave portion, a second concave portion, and a convex portion extending between the first concave portion and the second concave portion, wherein the first concave portion is adapted to seal against an interior surface of the first nostril, and wherein the second concave portion is adapted to seal against an interior surface of the second nostril,
   wherein the sealing portion comprises a first protruding portion and a second protruding portion each extending outwardly from the body, wherein the first concave portion coincides with the first protruding portion, and wherein the second concave portion coincides with the second protruding portion,
   wherein the sealing portion has an edge portion defining the opening, wherein the edge portion has a first peak point disposed in the first protruding portion, a second peak point disposed in the second protruding portion, and a bottom point disposed midway between the first peak point and the second peak point, wherein the edge portion has a first thickness proximate the first peak point, a second thickness proximate the second peak point, and a third thickness proximate the bottom point, and wherein the first thickness and the second thickness are less than the third thickness.

10. The cushion according to claim 9, wherein the edge portion further has a second convex portion extending between the first concave portion and the second concave portion, and wherein the second convex portion is disposed opposite, and is spaced from, the convex portion.

11. The cushion according to claim 9, wherein the edge portion is spaced a first distance from the first end of the cushion, wherein the edge portion is spaced a second distance from the second end of the cushion, and wherein the first distance is the same as the second distance.

12. A patient interface device for use in a pressure support system, the pressure support system comprising a gas flow generator structured to generate a flow of breathing gas to be delivered to an airway of a patient, the patient interface device comprising:

the cushion comprising:
 a body comprising a first end and a second end disposed opposite the first end, the body defining a space therein, and
 a sealing portion defining a single opening into the space, the single opening being adapted to surround both a first nostril and a second nostril of a patient, the sealing portion being disposed between the first end and the second end, the sealing portion comprising an edge portion defining the opening, the edge portion having a first concave portion, a second concave portion, and a convex portion extending between the first concave portion and the second concave portion, wherein the first concave portion is adapted to seal against an interior surface of the first nostril, and wherein the second concave portion is adapted to seal against an interior surface of the second nostril; and a conduit coupled to the first end of the cushion and structured to be coupled to the gas flow generator, the conduit being structured to provide a passage for the flow of breathing gas from the gas flow generator to the first end of the cushion, wherein the sealing portion comprises a first protruding portion and a second protruding portion each extending outwardly from the body, wherein the first concave portion coincides with the first protruding portion, and wherein the second concave portion coincides with the second protruding portion, wherein the sealing portion has an edge portion defining the opening, wherein the edge portion has a first peak point disposed in the first protruding portion, a second peak point disposed in the second protruding portion, and a bottom point disposed midway between the first peak point and the second peak point, wherein the edge portion has a first thickness proximate the first peak point, a second thickness proximate the second peak point, and a third thickness proximate the bottom point, and wherein the first thickness and the second thickness are less than the third thickness.

13. The patient interface device according to claim 12, wherein the conduit forms a portion of a headgear, and wherein the conduit is further coupled to the second end of the cushion in order to provide a passage for the flow of breathing gas from the gas flow generator to the second end of the cushion.

* * * * *